(12) United States Patent
Suda

(10) Patent No.: US 8,092,376 B2
(45) Date of Patent: Jan. 10, 2012

(54) LIGHT SOURCE DEVICE OF ENDOSCOPE SYSTEM

(75) Inventor: Tadaaki Suda, Saitama (JP)

(73) Assignee: Hoya Corporation, Tokyo (JP)

( * ) Notice: Subject to any disclaimer, the term of this patent is extended or adjusted under 35 U.S.C. 154(b) by 965 days.

(21) Appl. No.: 12/052,026

(22) Filed: Mar. 20, 2008

(65) Prior Publication Data
US 2008/0232130 A1 Sep. 25, 2008

(30) Foreign Application Priority Data
Mar. 23, 2007 (JP) ................. 2007-076276

(51) Int. Cl.
*A61B 1/06* (2006.01)
*A61B 3/00* (2006.01)
*F21V 5/00* (2006.01)
*G02B 6/06* (2006.01)
*G03B 15/02* (2006.01)
*G03B 29/00* (2006.01)

(52) U.S. Cl. ........................... 600/178; 362/574
(58) Field of Classification Search .......... 348/68–70; 362/574; 600/160, 178, 180, 199
See application file for complete search history.

(56) References Cited

U.S. PATENT DOCUMENTS

| | | | | |
|---|---|---|---|---|
| 3,026,449 A | * | 3/1962 | Rappaport | 315/166 |
| 4,782,386 A | * | 11/1988 | Ams et al. | 348/68 |
| 4,885,634 A | * | 12/1989 | Yabe | 348/71 |
| 6,293,911 B1 | * | 9/2001 | Imaizumi et al. | 600/160 |
| 6,734,893 B1 | * | 5/2004 | Hess et al. | 348/68 |
| 2004/0095464 A1 | * | 5/2004 | Miyagi et al. | 348/65 |
| 2007/0093688 A1 | | 4/2007 | Enomoto | |
| 2007/0112253 A1 | | 5/2007 | Negishi | |
| 2007/0225567 A1 | | 9/2007 | Kobayashi | |
| 2007/0253215 A1 | | 11/2007 | Takahashi et al. | |
| 2007/0263406 A1 | | 11/2007 | Negishi | |
| 2007/0265504 A1 | * | 11/2007 | Ott | 600/199 |

FOREIGN PATENT DOCUMENTS
JP 2000-166867 6/2000

OTHER PUBLICATIONS

English language Abstract of JP 2000-166867.
U.S. Appl. No. 12/052,029 to Suda, filed Mar. 20, 2008.
U.S. Appl. No. 12/052,030 to Ohtaki, filed Mar. 20, 2008.

* cited by examiner

*Primary Examiner* — Philip R Smith
(74) *Attorney, Agent, or Firm* — Greenblum & Bernstein, P.L.C.

(57) ABSTRACT

A light source device of an endoscope system comprises a light source and a light-source controller. The light source emits in a flash-emitting mode that the light source flashes in a flash interval longer than a field period of an imaging sensor for the endoscope system and for a flash period shorter than the field period. The light-source controller controls the light source so that the light source emits in the flash-emitting mode within an imaging period that is a period excluding a reading period within the field period. The flash interval is defined as a period from when the flash of the light source commences to when the next flash of the light source commences. The flash period is defined as a period from when the flash of the light source commences to when the flash of the light source is completed.

7 Claims, 5 Drawing Sheets

LIGHT SOURCE DEVICE OF ENDOSCOPE SYSTEM

BACKGROUND OF THE INVENTION

1. Field of the Invention

The present invention relates to a light source device of an endoscope system and in particular to a light source device that flashes in speed-light photography.

2. Description of the Related Art

An endoscope system that has an electronic scope including an imaging sensor is proposed.

Japanese unexamined patent publication (KOKAI) No. 2000-166867 discloses an endoscope system that has a light source device that flashes in speed-light photography in order to observe a moving subject or one that vibrates at a particular frequency, such as vocal cords. By flashing, it is possible to photograph a subject that vibrates with a cycle shorter than the imaging cycle (the field period of the imaging unit), in an apparently stationary state.

However, in that endoscope system, the cyclical timing of the flash does not take into account the non-imaging periods in which the captured image is read out. Therefore, the flash occasionally overlaps with the non-imaging period resulting in underexposed frames and flickering.

SUMMARY OF THE INVENTION

Therefore, an object of the present invention is to provide a light source device for an endoscope system that flashes within the imaging period in speed-light photography.

According to the present invention, a light source device of an endoscope system comprises a light source and a light-source controller. The light source emits in a flash-emitting mode that the light source flashes in a flash interval longer than a field period of an imaging sensor for the endoscope system and for a flash period shorter than the field period. The light-source controller controls the light source so that the light source emits in the flash-emitting mode within an imaging period that is a period excluding a reading period within the field period. The flash interval is defined as a period from when the flash of the light source commences to when the next flash of the light source commences. The flash period is defined as a period from when the flash of the light source commences to when the flash of the light source is completed.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
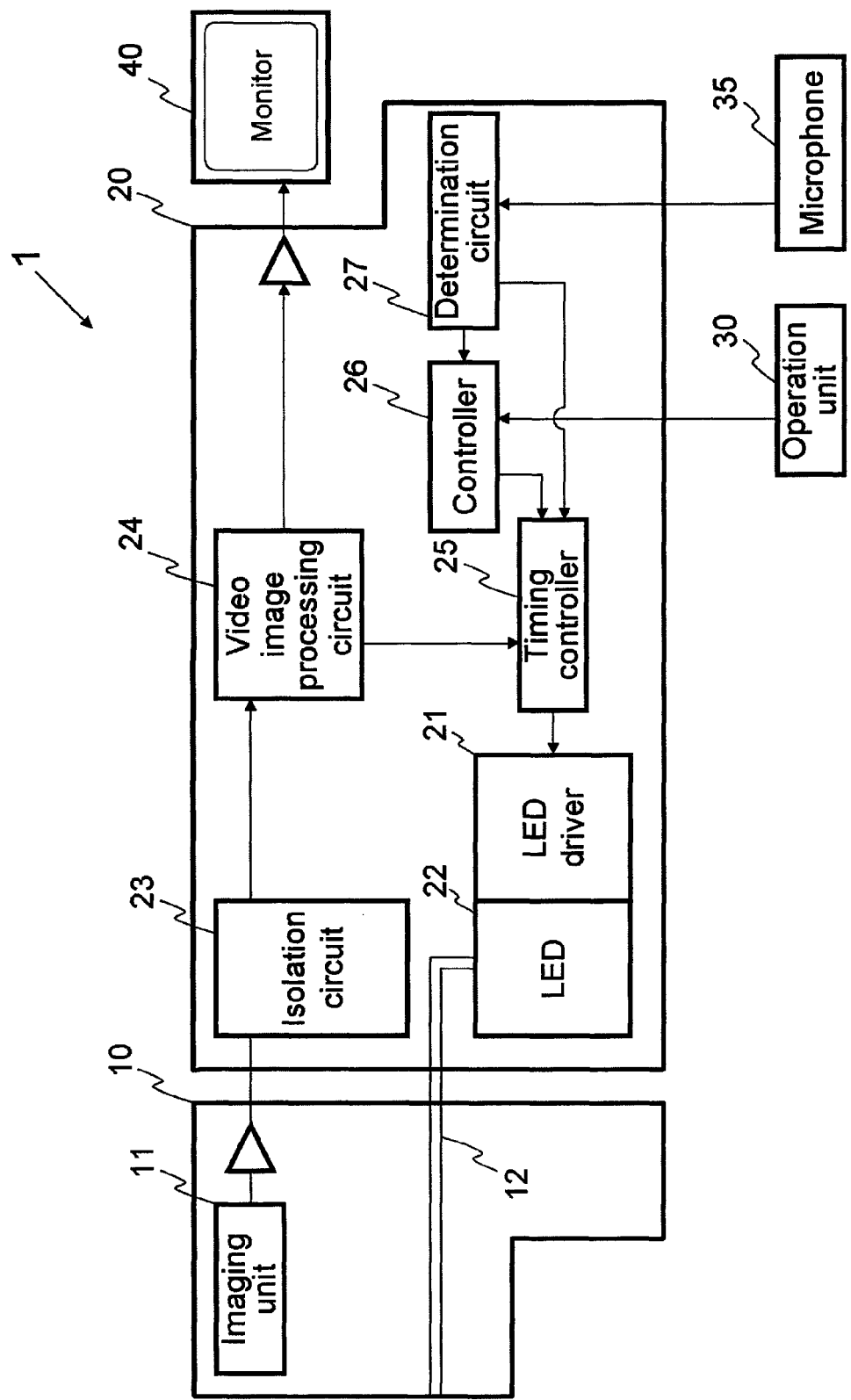
FIG. 1 is a construction diagram of the endoscope system.

The present invention is described below with reference to the embodiment shown in the drawings. As shown in FIG. 1, an endoscope system 1 in the embodiment comprises an electronic scope 10, an image processor 20, an operation unit 30, a microphone 35, and a monitor 40.

The electronic scope 10 has an insertion part and an operation-connection part. The insertion part is a flexible tube and is inserted into the body of a patient. The tip of the insertion part has an imaging unit 11 that has an imaging sensor and a control circuit for the imaging sensor. The operation-connection part has an operation key and is connected to the image processor 20.

During operation, the operator of the electronic scope 10 holds the operation-connection part and operates the operation key of the operation-connection part.

The electronic scope 10 has a light guide 12 that guides light from the image processor 20 to the tip of the insertion part through the operation-connection part.

The image processor 20 has an LED driver 21, an LED 22, a timing controller 25, a controller 26, and a determination circuit 27, together making up the light-source unit. In the embodiment, there are two types of emitting modes for the LED 22.

The normal emitting mode is an emitting mode in which the LED 22 emits full-time, or emits in a predetermined time interval, in the course of normal observation of the body.

The flash-emitting mode is an emitting mode in which the LED 22 flashes in speed-light photography, in order to observe a moving subject or one that vibrates at a particular frequency, such as vocal cords. By flashing, it is possible to photograph a subject that vibrates with a cycle shorter than the imaging cycle (a field period of the imaging unit 11), such as the vocal cords, in an apparently stationary state.

The image processor 20 also has an isolation circuit 23 and a video-image processing circuit 24. The image processor 20 performs image-processing on the image signal obtained by the electronic scope 10 so that the image corresponding to the image signal can be displayed on the monitor 40.

The operation unit 30, the microphone 35, and the monitor 40 are connected to the image processor 20. The operation unit 30 is an input device used for setting a flash interval $t_1$ and a flash period $t_2$ for the flash of the LED 22. Furthermore, either the normal emitting mode or the flash-emitting mode is selected by using the operation unit 30. When the flash-emitting mode is selected, the timing controller 25 is set to a mode for the flash of the LED 22.

The flash interval $t_1$ is defined as the period from when the flash of the LED 22 commences to when the next flash of the LED 22 commences.

The flash period $t_2$ is defined as the period from when the flash of the LED 22 commences to when the flash of the LED 22 is completed.

The microphone 35 is used for inputting a voice signal emitted by the vocal cords of the subject. The monitor 40 displays the image in conformity with the code of the predetermined video signal, upon which the image-processing is performed by the image processor 20.

The external memory that stores the image data, etc., based on the image signal that the image-processing is performed by the image processor 20, may be connected to the image processor 20. Furthermore, the printer, that outputs the image based on the image signal that the image-processing is performed by the image processor 20, may be connected to the image processor 20.

Next, the details of the endoscope system 1 are explained.

The light emitted by the LED 22 is cast on the subject through the light guide 12 which is provided in the electronic scope 10 and has many optical fibers.

In the embodiment, the image processor 20 includes the light-source unit such as the LED driver 21 and the LED 22, etc. However, the light-source unit may be separate from the image processor 20.

Furthermore, the light source of the light-source unit is not limited to the LED, such as in the case that the light source is used to emit in both normal emitting mode and flash-emitting mode.

The LED 22 is driven by the LED driver 21 that is controlled by the controller 26.

In the normal emitting mode, the driver 21 drives the LED 22 by continuous passage of electric current to the LED 22, in other words, by a current drive. Or, the driver 21 may drive the LED in a pulse drive based on the supply of a pulse train made of pulses with a time interval shorter than the field period $t_0$.

In the flash-emitting mode, the driver 21 drives the LED 22 in a pulse drive based on the supply of a pulse train made of pulses with the flash interval $t_1$ longer than the field period $t_0$ and with a short pulse width that is the flash period $t_2$.

The reflection of the subject based on the illumination of the endoscope system 1 reaches the imaging sensor of the imaging unit 11 through the objective optical system (not depicted), and the optical image of the subject is imaged on the incident surface of the imaging sensor of the imaging unit 11. At the imaging sensor, the photoelectric conversion operation of the optical image is performed and then the image signal based on the optical image is output.

The image signal output from the imaging unit 11 is amplified and then is transmitted to the video-image processing circuit 24 of the image processor 20 through the isolation circuit 23. The video-image processing circuit 24 performs the image signal processing operation of the image signal and then temporarily stores the image data based on the image signal to the memory (not depicted). The isolation circuit 23 protects the patient from the electric shock, etc.

The image data temporarily stored in the memory of the video processing circuit 24 is read in order to perform the video signal processing operation in conformity with the code of the predetermined video signal and then output to the monitor 40. Thus, an image corresponding to the subject is displayed on the monitor 40.

The timing controller 25 controls the drive timing of the LED driver 21 that drives the LED 22 in the flash-emitting mode. The timing controller 25 is controlled by the controller 26.

Specifically, the timing controller 25 controls the drive timing of the LED driver 21 so that the LED 22 flashes in the flash interval $t_1$ and for the flash period $t_2$ set by the operator, on the basis of the detection of the voice signal by the determination circuit 27 from the microphone 35.

Therefore, the LED driver 21, the timing controller 25, and the controller 26 working as a light-source controller, direct the LED 22 to flash in the flash-emitting mode.

Furthermore, the timing controller 25 controls the drive timing of the LED driver 21 so that the LED 22 flashes within an imaging period. The imaging period is the period excluding the reading period TR within the field period $t_0$. The reading period TR is the non-imaging period during which the accumulated electric charge in the imaging sensor is read.

Figure 5:
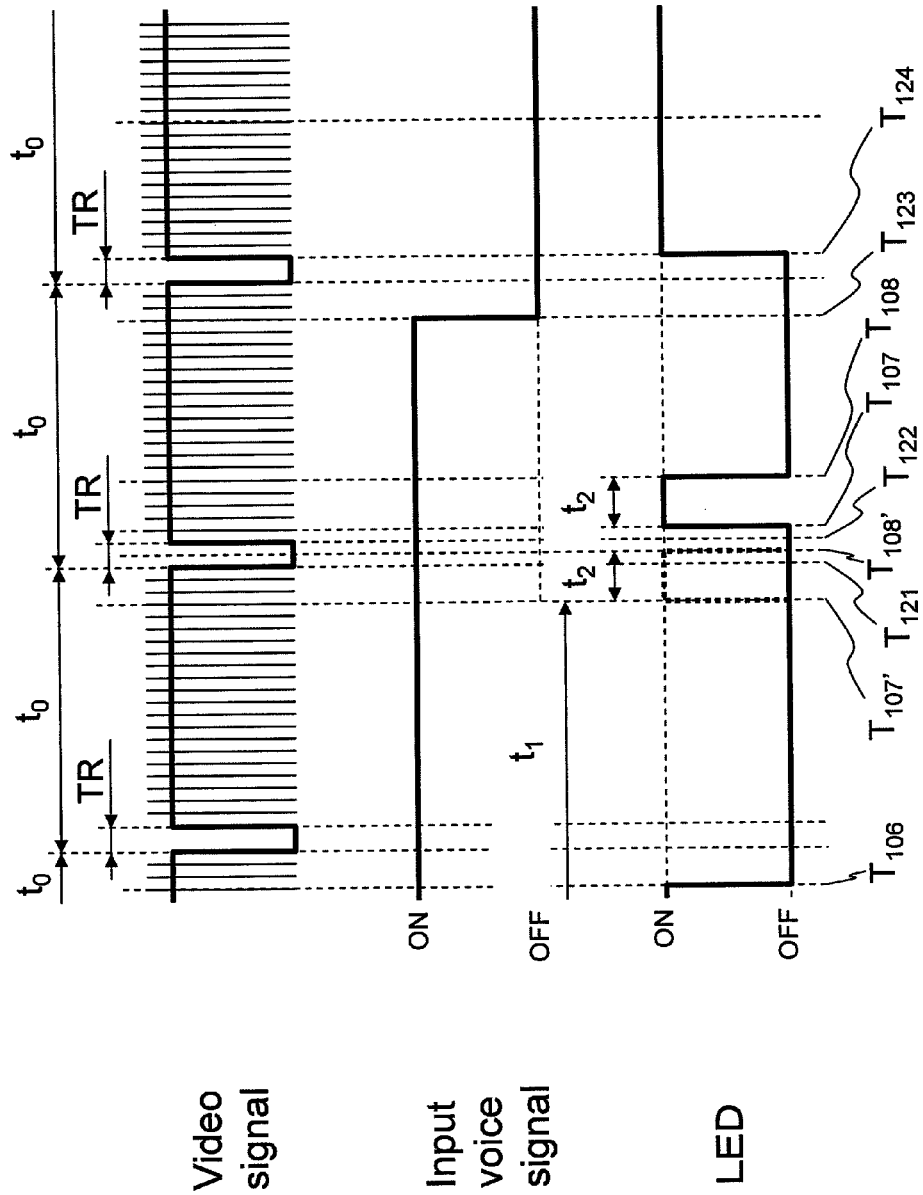
FIG. 5 is a timing chart that shows a flow where the flash-emitting mode changes to the normal emitting mode again.

Specifically, when either the first time point at the commencement of the next flash of the LED 22 or the second time point at the completion of the next flash of the LED 22 overlaps with the reading period TR, the flash of the LED 22 is stopped until the completion of this reading period TR and recommences after completion of the reading period TR (see FIG. 5). The first time point at the commencement of the next flash of the LED 22 is defined as the time point when the flash interval $t_1$ has elapsed after the commencement of the flash of the LED 22. The second time point at the completion of the next flash of the LED 22 is defined as the time point when the flash period $t_2$ has elapsed after the commencement of the next flash of the LED 22.

Furthermore, the timing controller 25 controls the LED driver 21 so that the commencement of the flash of the LED 22 is set to the middle of the field period $t_0$ so that at least part of the flash period $t_2$ will not overlap with the reading period TR, when the flash interval $t_1$ set by the operator is close in length to the field period $t_0$.

The timing controller 25 has a field-period check timer Fi(t), a flash-interval check timer Si(t), and a flash-period check timer Sr(t).

The flash-interval check timer Fi(t) is used for counting a first elapsed time of the field period $t_0$ on the video signal obtained by the imaging unit 11, in order to control the drive timing of the LED driver 21.

The flash-interval check timer Si(t) is used for counting a second elapsed time of the flash interval $t_1$ of the LED 22 in the flash-emitting mode.

The flash-period check timer Sr(t) is used for counting a third elapsed time of the flash period $t_2$ of the LED 22 in the flash-emitting mode.

The initial value of the field-period check timer Fi(t), that is, its value at the starting time point of the field period $t_0$, is set to the value of the field period $t_0$. The starting time point of the field period $t_0$ is equal to the starting time point of the reading period TR.

The value of the field-period check timer Fi(t) is decreased by the elapsed time, in order to count down the first elapsed time. At the starting time point of the next field period, the value of the field-period check timer Fi(t) is reset, in other words, it is set to 0 and then set to the initial value of the field period $t_0$.

The control of the reset timing of the value of the field-period check timer Fi(t) is performed on the basis of the transfer pulse of the control signal of the imaging unit 11 that is transferred through the video-image processing circuit 24.

The initial value of the flash-interval check timer Si(t), that is, its value at the starting time point of the flash of the LED 22, is set to the value of the flash interval $t_1$.

The value of the flash-interval check timer Si(t) is also decreased by the elapsed time, in order to count down the second elapsed time. At the time point of the commencement of the next flash of the LED 22, the value of the flash-interval check timer Si(t) is reset, in other words, it is set to 0 and then set to the initial value of the flash interval $t_1$.

The initial value of the flash-period check timer Sr(t), that is, its value at the starting time point of the flash of the LED 22, is set to the value of the flash period $t_2$.

The value of the flash-period check timer Sr(t) is decreased by the elapsed time, in order to count down the third elapsed time. At the time point of the completion of the flash period $t_2$ of the LED 22, the value of the flash-period check timer Sr(t) is reset, in other words, it is set to 0 and then set to the initial value of the flash period $t_2$.

The controller 26 is a microprocessor, or the like, that controls all parts of the electronic scope 10 and the image processor 20. The controller 26 outputs a signal indicating whether the operation unit 30 is being operated so that the LED 22 flashes in the flash-emitting mode, to the timing controller 25.

The determination circuit 27 detects the voice signal emitted by the vocal cords of the subject, that arrives at the microphone 35.

Specifically, the determination circuit 27 determines whether the signal level input to the microphone 35 is greater than or equal to the predetermined threshold value.

When this condition is met, the determination circuit 27 determines that a voice signal has been input to the microphone 35, and this result is transferred to the timing controller 25 and the controller 26.

While the voice signal is input to the microphone 35, the LED 22 flashes in the flash-emitting mode.

Figure 2:
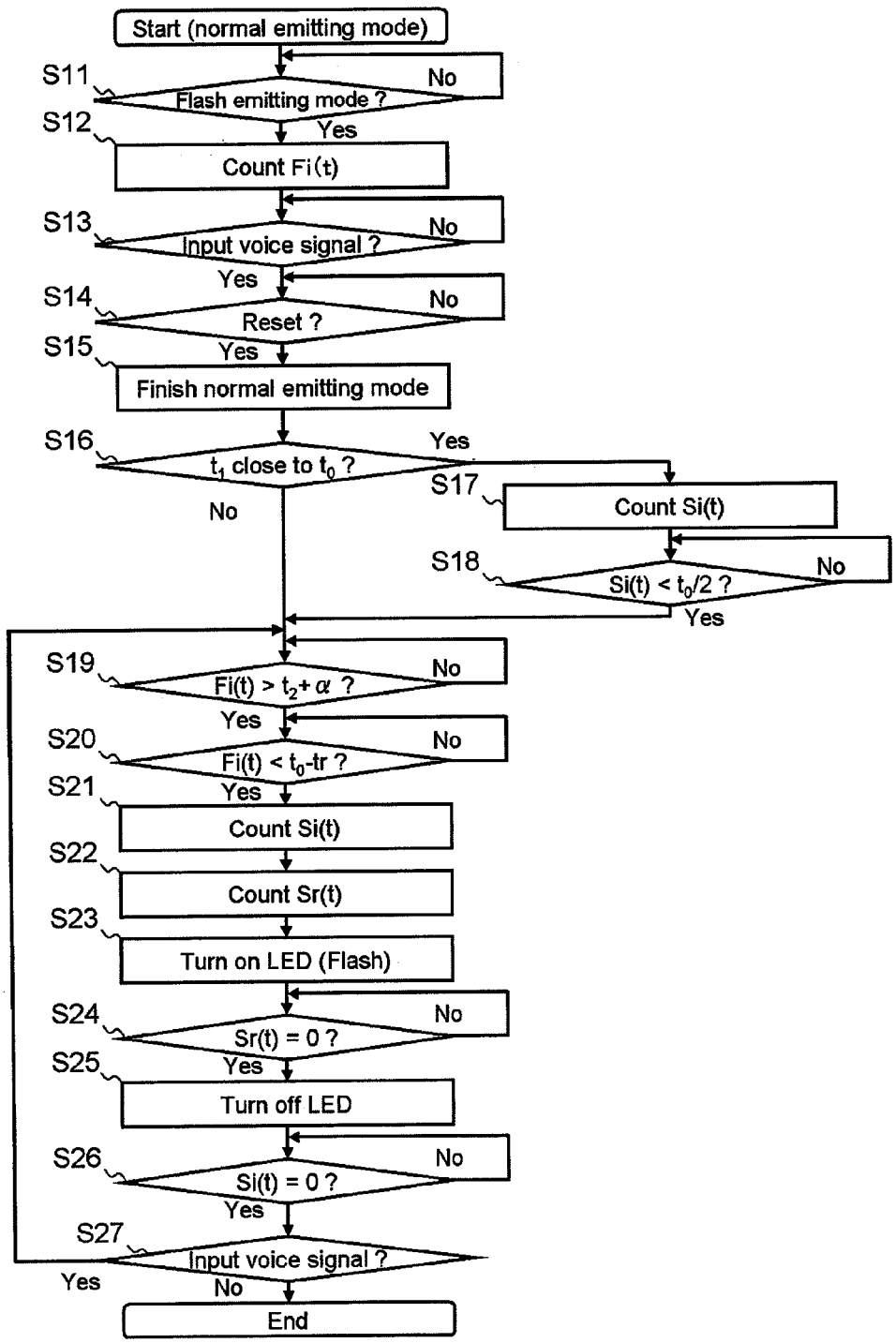
FIG. 2 is a flowchart that shows a flow where the normal emitting mode changes to the flash-emitting mode and then changes to the normal emitting mode.
Figure 3:
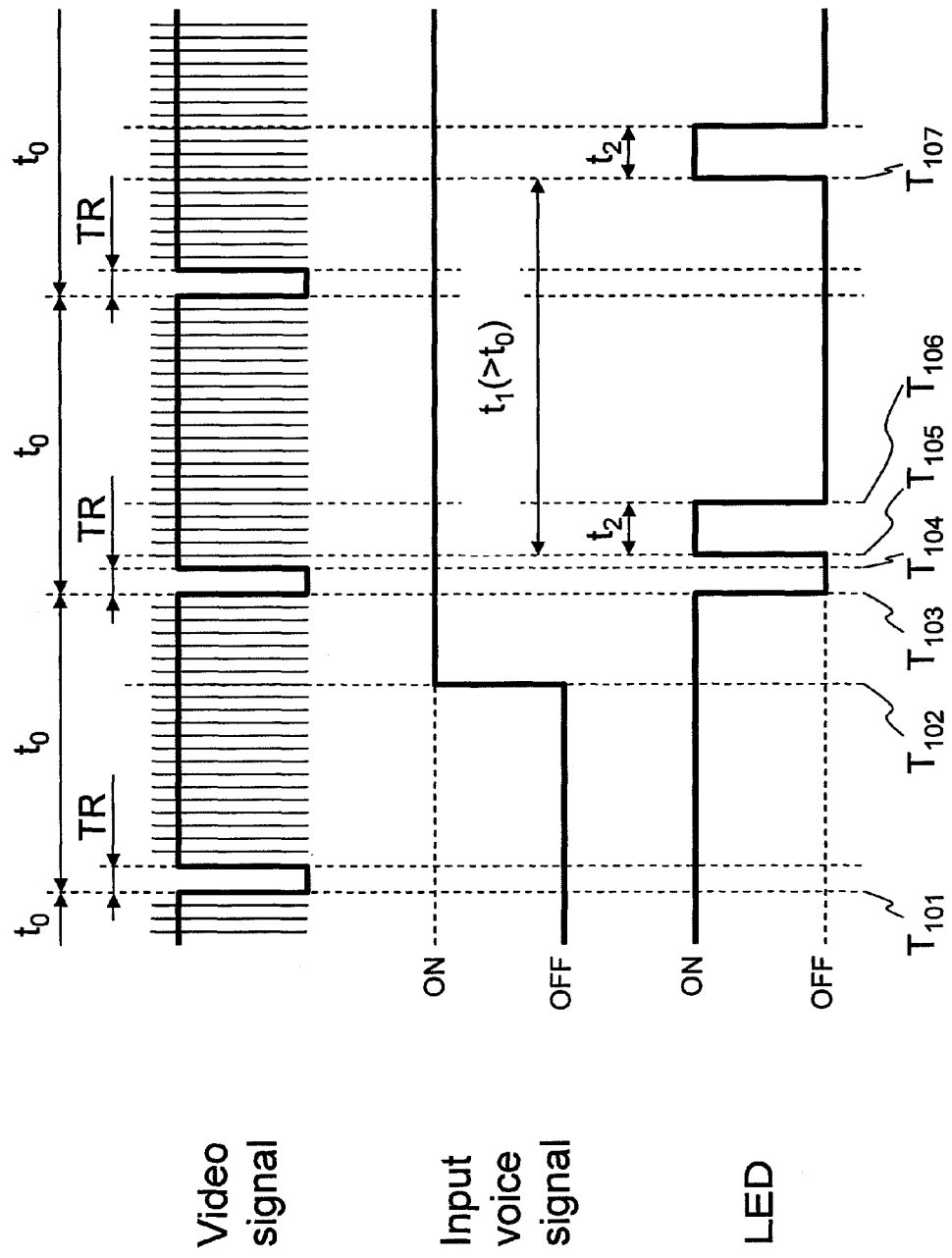
FIG. 3 is a timing chart that shows a flow where the normal emitting mode changes to the flash-emitting mode, when the timing of the commencement of the LED flash is not delayed.
Figure 4:
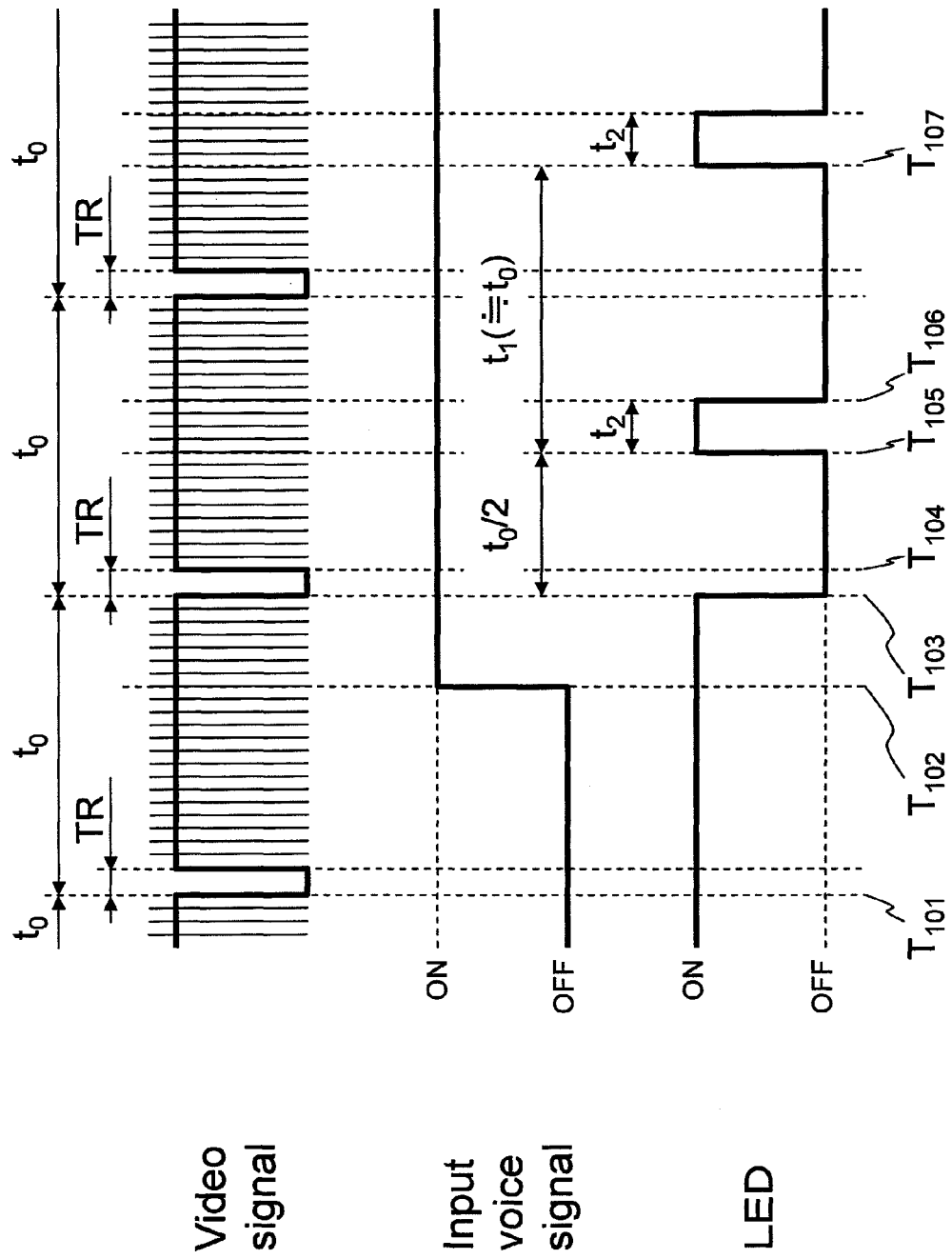
FIG. 4 is a timing chart that shows a flow where the normal emitting mode is changed to the flash-emitting mode, when the timing of the commencement of the LED flash is delayed.

Next, the flow where the normal emitting mode changes to the flash-emitting mode and then back to the normal emitting mode is explained using the flowchart in FIG. 2, and the timing charts in FIGS. 3 to 5.

The LED 22 is driven by the current drive or the pulse drive, and emits in the normal emitting mode. Then, in step S11, it is determined whether the operator has set the flash-emitting mode by operating the operation unit 30 so that the timing controller 25 is prepared for driving the LED driver 21 in the flash-emitting mode.

When it is determined that the timing controller 25 is ready to drive the LED driver 21 in the flash-emitting mode, the operation continues to step S12, otherwise, the operation in step S11 is repeated.

In step S12, counting down of the first elapsed time based on the field-period check timer Fi(t) commences, together with the reset timing of the transfer pulse (see the time point $T_{101}$ in FIGS. 3 and 4).

In step S13, it is determined whether the voice signal input to the microphone 35 has been detected by the determination circuit 27, in other words, whether the voice signal is input through the microphone 35. When it is determined that the voice signal input to the microphone 35 is detected by the determination circuit 27 (see the time point $T_{102}$ in FIGS. 3 and 4), the operation continues to step S14, otherwise, the operation in step S13 is repeated.

In step S14, it is determined whether the field period is completed so that the value of the field-period check timer Fi(t) has been reset by the transfer pulse. When it is determined that the value of the field-period check timer Fi(t) is reset (see the time point $T_{103}$ in FIGS. 3 and 4), the operation continues to step S15, otherwise, the operation in step S14 is repeated.

In step S15, emission of the LED 22 in the normal emitting mode finishes, in other words, the LED 22 in the normal emitting mode is turned off (see the time point $T_{103}$ in FIGS. 3 and 4).

The emission of the LED 22 in the normal emitting mode finishes by the completion of the field period $t_0$ including the time point when the voice signal input is detected.

In the next field period, the flash of the LED 22 in the flash-emitting mode commences.

In step S16, it is determined whether the value of the flash interval $t_1$ set by the operation unit 30 by the operator is close to the value of the field period $t_0$, in other words, it is determined whether the difference between the flash interval $t_1$ and the field period $t_0$ is less than or equal to 5% of the field period $t_0$.

When it is determined that the value of the flash interval $t_1$ is close to the value of the field period $t_0$ (see FIG. 4), the operation continues to step S17 to reduce the opportunity for part of the flash period $t_2$ to overlap with the reading period TR, otherwise (see FIG. 3), the operation proceeds directly to step S19.

In step S17, counting down of the second elapsed time based on the flash-interval check timer Si(t) commences (see the time point $T_{103}$ in FIG. 4).

In step S18, it is determined whether the value of the flash-interval check timer Si(t) is less than half the value of the field period $t_0$. When it is determined that the value of the flash-interval check timer Si(t) is less than half the value of the field period $t_0$ (Si(t)<$t_0$÷2), the operation continues to step S19, otherwise (Si(t)≧$t_0$÷2), the operation in step S18 is repeated. Thus, the flash of the LED 22 does not commence until half the duration of the field period $t_0$ has elapsed after commencing at the time point $T_{103}$ of FIG. 4.

In step S19, it is determined whether the value of the field-period check timer Fi(t) is greater than the sum of the flash period $t_2$ and a processing time α for emitting the LED 22 (α<<$t_2$). When it is determined that the value of the field-period check timer Fi(t) is greater than the sum of the flash period $t_2$ and the processing time (Fi(t)>$t_2$+α), the operation continues to step S20, otherwise (Fi(t)≦$t_2$+α), the operation in step S19 is repeated. Thus, the flash period $t_2$ is completed by the completion of the field period $t_0$, in other words, the overlap of part of the flash period $t_2$ with the reading period TR is prevented. In other words, when at least part of the next flash period $t_2$ ($T_{107'}$ to $T_{108'}$ in FIG. 5), that is calculated based on the relationship between the time point $T_{105}$ in FIGS. 3 and 4 when the flash of the LED 22 commenced and the flash interval $t_1$, overlaps with the reading period TR ($T_{121}$ to $T_{122}$ in FIG. 5), the flash of the LED 22 commences at the time point $T_{107}$ after the time point $T_{122}$ of the completion of the reading period TR.

In step S20, it is determined whether the value of the field-period check timer Fi(t) is less than the difference between the field period $t_0$ and the reading period TR. When it is determined that the value of the field-period check timer Fi(t) is less than the difference between the field period $t_0$ and the reading period TR (Fi(t)<$t_0$−TR), the operation continues to step S21, otherwise (Fi(t)≧$t_0$−TR), the operation in step S20 is repeated.

Thus, the flash of the LED 22 is prevented from commencing in the reading period TR, in other words, in the period from the time point $T_{103}$ in FIGS. 3 and 4 that is the starting time point of the field period $t_0$ (the starting time point for counting the field-period check timer Fi(t)) to the time point $T_{104}$ in FIGS. 3 and 4 that is the time point of the completion of the reading period TR.

In step S21, counting down of the second elapsed time based on the flash-interval check timer Si(t) commences.

In step S22, counting down of the third elapsed time based on the flash-period check timer Sr(t) commences.

In step S23, the flash of the LED 22 commences (see the time point $T_{105}$ in FIGS. 3 and 4).

In step S24, it is determined whether the value of the flash-period check timer Sr(t) is 0, in other words, it is determined whether the flash period $t_2$ has elapsed from when the flash of the LED 22 commenced. When it is determined that the value of the flash-period check timer Sr(t) is 0 (see the time point $T_{106}$ in FIGS. 3 and 4), the operation continues to step S25, otherwise, the operation in step S24 is repeated.

In step S25, the flash of the LED 22 is completed, in other words, the LED 22 is turned off.

In step S26, it is determined whether the value of the flash-interval check timer Si(t) is 0, in other words, whether the flash interval $t_1$ has elapsed from when the flash of the LED 22 commenced. When it is determined that the value of the flash-interval check timer Si(t) is 0 (see the time point T107 in FIGS. 3 to 5), the operation continues to step S27, otherwise, the operation in step S26 is repeated.

In step S27, it is determined whether the voice signal input to the microphone 35 has been detected by the determination circuit 27. While it is the case that the voice signal input to the microphone 35 is detected by the determination circuit 27, the operation returns to step S19 so that the operation in steps S19 to S27 is repeated, otherwise (see the time point $T_{123}$ in FIG. 5), emission of the LED 22 in the flash-emitting mode is finished, in other words, the LED 22 in the flash-emitting mode is turned off. From the time point of the completion of the reading period TR in the next field period (see the time point $T_{124}$ in FIG. 5), the flash of the LED 22 in the normal emitting mode commences.

In the case that the flash of the LED 22 in the flash-emitting mode is performed without considering the reading period TR in the field period $t_0$, the LED 22 may flash concurrently with the reading period TR so that the imaging operation is performed with insufficient light.

In the embodiment, control of emission of the LED 22 is performed so that the LED 22 flashes within the imaging period without overlapping the reading period TR in the field period $t_0$.

Therefore, the imaging operation can be performed continuously with the LED 22 flashing sufficiently within the imaging period and in a time interval close to the flash interval $t_1$. As a consequence flicker, in which the whole image displayed on the monitor 40 brightens or darkens suddenly, does not tend to occur, allowing comfortable viewing of the image displayed on the monitor 40.

Although the embodiment of the present invention has been described herein with reference to the accompanying drawings, obviously many modifications and changes may be made by those skilled in this art without departing from the scope of the invention.

The present disclosure relates to subject matter contained in Japanese Patent Application No. 2007-076276 (filed on Mar. 23, 2007) which is expressly incorporated herein by reference, in its entirety.

The invention claimed is:

1. A light source device of an endoscope system comprising:
   a light source that emits in a flash-emitting mode, wherein said light source flashes in a flash interval that is longer than a field period of an imaging sensor for said endoscope system and for a flash period that is shorter than said field period; and
   a light-source controller that controls said light source so that said light source prevents emission in said flash-emitting mode within a reading period that is a period excluding an image period within said field period;
   said flash interval being defined as a period from when the flash of said light source commences to when the next flash of said light source commences, and said flash period being defined as a period from when the flash of said light source commences to when the flash of said light source is completed.

2. The light source device according to claim 1, wherein said light-source controller controls said light source so that said light source emits in said flash-emitting mode within said imaging period, on the basis of a first elapsed time of said field period, a second elapsed time of said flash interval in said flash-emitting mode, and a third elapsed time of said flash period.

3. The light source device according to claim 1, further comprising a detector that detects a voice signal input;
   wherein said light-source controller turns off said light source that is emitting in a normal emitting mode by the completion of a first field period including a time point when said detector detects said input of said voice signal, and controls said light source in said flash-emitting mode starting from a second field period that is the next field period of said first field period.

4. The light source device according to claim 3, wherein said light-source controller controls said light source in said flash-emitting mode so that a timing of the commencement of the flash of said light source is set to a middle of said field period when said flash interval is close in length to a length of said field period.

5. The light source device according to claim 4, wherein said light-source controller controls said light source in said flash-emitting mode so that the flash of said light source is stopped until a completion of said reading period and commences after completion of said reading period, when at least one of a first time point and a second time point overlaps with said reading period;
   said first time point is the time point when said flash interval has elapsed after the commencement of the flash of said light source; and
   said second time point is the time point when said flash period has elapsed after said first time point.

6. The light source device according to claim 1, said light source controller being configured so that in said flash emitting mode, when a length said flash interval is within a predetermined percentage of a length of said field period, commencement of the flash of said light source is controlled to occur at a middle of said field period.

7. The light source device according to claim 1, wherein said light source controller controls light source in the flash emitting mode so that the flash of said light source is stopped until a completion of said reading period and commences after completion of said reading period, when at least one of a first-time point and a second time point overlap with said reading period, said first-time point being the time point when said flash interval has elapsed after the commencement of the flash of the light source; and said second time point is the time point when said flash period has elapsed after said first-time point.

\* \* \* \* \*